(12) United States Patent
Benson (10) Patent No.: US 6,878,517 B1
(45) Date of Patent: Apr. 12, 2005

(54) MULTISPECIES FOOD TESTING AND CHARACTERIZATION ORGANOLEPTIC PROPERTIES

(75) Inventor: Andrew K. Benson, Lincoln, NE (US)

(73) Assignee: Congra Grocery Products Company, Irvine, CA (US)

( * ) Notice: Subject to any disclaimer, the term of this patent is extended or adjusted under 35 U.S.C. 154(b) by 0 days.

(21) Appl. No.: 09/639,690

(22) Filed: Aug. 16, 2000

Related U.S. Application Data (60) Provisional application No. 60/171,004, filed on Dec. 15, 1999.

(51) Int. Cl.[7] .......................... C12Q 1/68; C12N 15/00; G06F 19/00; C12M 1/34; C07H 21/04
(52) U.S. Cl. .............................. 435/6; 435/7.1; 435/8; 435/283.1; 435/287.1; 435/287.2; 702/19; 702/20; 536/23.1
(58) Field of Search ................................ 435/6, 29, 7.1, 435/8, 283.1, 287.1, 287.2; 702/19, 20; 536/23.1

(56) References Cited

U.S. PATENT DOCUMENTS

| | | | | |
|---|---|---|---|---|
| 5,795,717 A | * | 8/1998 | Nakayama et al. | ............ 435/6 |
| 5,874,046 A | * | 2/1999 | Megerle | |
| 5,922,591 A | * | 7/1999 | Anderson et al. | ......... 435/287.2 |
| 6,001,564 A | * | 12/1999 | Bergeron et al. | ............... 435/6 |
| 6,057,100 A | * | 5/2000 | Heyneker | ...................... 435/6 |
| 6,083,763 A | * | 7/2000 | Balch | |

FOREIGN PATENT DOCUMENTS

WO    WO 98/28444    7/1998

OTHER PUBLICATIONS

Bruckner–Lea et al. Strategies for automated sample preparation, nucleic acid purification, and concentration of low target number nucleic acids in environmental and food processing samples. Proc. SPIE–Int. Soc. Opt. Eng. 1999, vol. 3544, pp. 63–71.*

Tauxe. Emerging foodborne diseases: an evolving public health challenge. Emergins Infectious Diseases. 1997, vol. 3, pp. 425–434.*

Bruckner, Cynthia J. et al. "Strategies for Automated Sample Preparation, Nucleic Acid Purification, and Concentration of Low Target Number Nucleic Acids in Environmental and Food Processing Samples" Part of the SPIE Conference on Pathogen Detection and Remediation for Safe Eating, Boston, Massachusetts 1998 p. 63–71, SPIE vol. 3544.

de Boer, Enne et al. "Method for detection and typing of foodborne microorganisms," International Journal of Food Microbiology 50 (1–2):119–130 (1999).

(Continued)

*Primary Examiner*—Gerry Leffers
(74) *Attorney, Agent, or Firm*—Nutter McClennen & Fish LLP (57) ABSTRACT

A testing system useful for food products employs a multispecies testing array to test for presence or amount of a plurality of organisms in a sample by detecting plural characteristic sequences for each of plural organisms to form a multispecies distribution output or microbial profile, and this is processed or used in conjunction with data mining or other processing to provide trend, warning or other data. The processor correlates and stores information relating to taste, smell, texture, processing conditions, quality or source of a component or ingredient, potential pathogenicity or other factor, with correlations on a multidimensional space yielding new preconditions or warning indications, and providing a mechanism for specialization of the species distribution data for specific products, as well as for incorporation or development of process changes and company trade secrets.

23 Claims, 5 Drawing Sheets

OTHER PUBLICATIONS

Guschin, Dmitry Y. et al. "Oligonucleotide Microchips as Genosensors for Determinative and Evironmental Studies in Microbiology," Applied and Environmental Microbiology, 63(6): 2397–2402 (1997).

Schena, Mark et al. "Microarrays: biotechnology's discovery platform for functional genomics", TIBTECH, 16(7): 301–306 (1998).

Troesch, A. et al. "Mycobacterium Species Identification and Rifampin Resistance Testing with High–Density DNA Probe Arrays," Journal of Clinical Microbiology, 37(1): 49–55 (1999).

van der Vossen, Jos M.B.M. "DNA based typing, identification and detection systems for food spoilage microorganisms: development and implementation," International Journal of Food Microbiology, 33: 35–49 (1996).

Winzeler, Elizabeth A. et al. "Fluorescence–Based Expression Monitoring Using Microarrays," Methods In Enzymology, 306: 3–18 (1999).

Carl A. Batt, Symposium: Molecular Probes—theory and application: Molecular diagnostics for diary–borne pathogens. J. Dairy Sci. 1997, vol. 80, pp. 220–229, see whole document.

S.L. Moseley et al., "Detection of Enterotoxigenic *Escherichia coli* by DNA Colony Hybridization" (*The Journal of Infectious Diseases*), vol. 142, No. 6, p. 892–898, (Dec. 1980).

M.N. Widjojoatmodjo et al. "Evaluation of the Magentic Immuno PCR Assay for Rapid Detection of *Salmonella*" (*Eur. J. Clin. Microbiol.Infect. Dis,*) p. 935–938 (Nov. 1991).

Randall K. Saiki et al., Primer–Directed Enzymatic Amplification of DNA with a Thermostable DNA Polymerase (*Science*) vol. 239, p. 487–491 (Jan. 1988).

Zhen Guo et al., "Deirec fluorescence analysis of genetic polymorhisms by hybridization with oligonucleotide arrays on glass supports" (*Nucleic Acids Research*) vol. 22, No. 24 p. 5456–5465 (1994).

A.R. Bennett et al. "The isolation and detection of *Escherichia coli*) O157 by use of immunomagnetic separation and immunoassay procedures" (*Letters in Applied Microbiology*) 22 p. 237–243 (1996).

W. King et al. "A new colorimetric nucleic acid hybridization assay for *Listeria* in foods" (*International Journal of Food Microbiology*) 8 p. 225–232 (1989).

Mark Chee et al., "Accessing Genetic Information with High–Density DNA Arrays" (*Science*) vol. 274 p. 610–614 (Oct. 1996).

Mary T. Bessesen et al. "Detection of *Listeria monocytogenes* by using the Polymerase Chain Reaction" (*Applied and Environmental Microbiology*) p. 2930–2932 (Sep. 1990).

Catherine W. Donnelly et al., "Method for Flow Cytometric Detection of *Listeria monocytogenes* in Milk" (*Applied and Environmental Microbiology*) p. 689–695 (Oct. 1986).

Dmitry Y. Guschin et al., "Oligonucleotide Microchips as Genosensors for Determinative and Environmental Studies in Microbiology" (*Applied and Environmental Microbiology*) p. 2397–2402 (Jun. 1997).

Katsunori Kimura et al., "Analysis of Fecal Populations of Bifidobacteria and Lactobacill and Investigation of the Immunological Responses of Their Human Hosts to the Predominant Strains" (*Applied and Environmental Microbiology*) p. 3394–3398 (Sep. 1997).

R.D. Oberst et al., "PCR–Based DNA Amplification and Presumptive Detection of *Escherichia coli* O157:H7 with an Internal Flurogenic Probe and the 5' Nuclease (TaqMan) Assay" (*Applied and Environmental Microbiology*) P. 3389–3396 (Sep. 1998).

Frank Schwieger et al. "A new approach to Utilize PCR–Single–Strand–Conformation Polymorphism for 16S rRNA Gene–Based Microbial Community Analysis" (*Applied and Environmental Microbiology*) p. 4870–4876 (Dec. 1998).

Antonia Suau et al. "Direct Analysis of Genes Encoding 16S rRNA form Complex Communities Reveals Many Novel Molecular Species within the Human Gut" (*Applied and Environmental Microbiology*) P. 4799–4807 (Nov. 1999).

\* cited by examiner

Gene target table for model array

| | A-B | C-D | E-F | G-H | I-J | K-L | M-N | O-P | Q-R | S-T | U-V | W-X |
|---|---|---|---|---|---|---|---|---|---|---|---|---|
| 1 Bacillus/Listeria | Bacillus Hemolysin BL | Bacillus Entero-toxin | Bacillus dacF | Bacillus spoIIGA | Bacillus sigE | Bacillus sigE | Bacillus Entero-Toxin A (hblB) | Bacillus spoOA | Bacillus spoIIAA | Listeria Ipa-p60 | Listeria ltrA | Listeria mpl |
| 2 Controls | Blank | Blank | Control gfp | Control gfp 1:10 | Control gfp 1:100 | Control gfp 1:1000 | | | Control gfp | Control gfp | | |
| 3 Campylobacter/Llisteria | Campy pglA | Campy cipA | Campy lig3 | Campy flaB | Campy ciaE | Campyb folP | Campy pglD | Campyl pglF | Campy pglB | Listeria InlB | Listeria hlyA | Listeria inlA |
| 4 E.coli/Listeria | E.coli asptRNA | E.coli 23sRNA | E.coli lacZ | E.coli thrtRNA | E.coli hylD | E.coli gdh | E.coli rpoS | E.coli uidA | E.coli alr | Listeria prfA | Listeria plcB | Listeria plcA |
| 5 Yersinia/O157 | Yersinia yopD | Yersinia yopB | Yersinia yopH | Yersinia yopE | Yersinia lcrV | Yersinia virF | Yersinia yopN | Yersinia yopP | Yersinia yopM | O157:H7 ehxA | O157:H7 hlyA | O157:H7 toxB |
| 6 Staphylococcus aureus/E. coli O157:H7 | S. aureus entG | S. aureus sarA | S. aureus entA | S. aureus entD | S. aureus nuclease | S. aureus seIlA | S. aureus agrB | S. aureus entI | S. aureus tsst-1 | O157:H7 espP | O157:H7 eaeA | O157:H7 etpC |
| 7 Shigella/E. coli O157:H7 | Shigella fur | Control gfp | Shigella icsB | Shigella stxA | Shigella ipaC | Shigella vacB | Control gfp | Shigella ipaB | Shigella virR | Shigella sod | Control gfp | Shigella virF |
| 8 Salmonella/E.coli O157:H7 | Salmonella sopE | Salmonella pagC | Salmonell invJ | Salmonell spiA | Salmonell prgK | Salmonell traJ | Salmonell traK | Salmonell invH | Salmonell traB | O157:H7 Rorf2 | O157:H7 stx2 | O157:H7 escT |

FIG. 4

FIG. 4A 1A-1R = *Bacillus cereus*
2A-2Z = controls
3A-3R = *Campylobacter jejuni*
4A-4R = *E. coli*
5A-5R = *Yersinia enterocolitica*
6A-6R = *Staphylococcus aureus*
7A-B, 7E-L, 7O-T, 7W-X = *Shigella dysenteriae*
8A-8R = *Salmonella enterica*

1S-1X = Listeria monocytogenes
2S-2X = controls (UV are positive controls)
3S-3X = Listeria monocytogenes
4S-4X = Listeria monocytogens
5S-5X = E. coli O157:H7
6S-6X = E. coli O157:H7
7C-D, 7M-N, 7U-V = controls (UV are + controls)
8S-8X = E. coli O157:H7

1000 cells 100 cells 10 cells

MULTISPECIES FOOD TESTING AND CHARACTERIZATION ORGANOLEPTIC PROPERTIES

This application claims the benefit of U.S. provisional 60/171,004 filed Dec. 15, 1999.

BACKGROUND

The present invention relates to bacteriological testing and to food processing.

Increasing publicity surrounding outbreaks of foodborne illness, and political pressure on the part of consumer groups have intensified the need for developing effective methods for detecting microorganisms in food and or eliminating them from the food chain. In the current climate of public awareness, a single outbreak of foodborne illness or even the identification of a contaminated product can be devastating. While pre-harvest and post-harvest intervention strategies are ultimately the best places to address microbial contamination, solutions at these levels will require long-term research commitments and may require implementation of substantial changes to the operation of food-growing enterprises. On the other hand, development of efficient testing methodologies may provide near-term solutions for reducing the amount of contaminated product that reaches the market. Despite the importance of this problem, state of the art testing methods remain limited in scope, are labor intensive, and are incapable of providing real-time information. The primary obstacles to fast and convenient testing are imposed by biophysical constraints on the system and sampling. In the absence of approaches to overcome these constraints in the near future, we are left with the question of how to upgrade current testing methodologies.

One clearly desirable goal for microbial monitoring systems would be the development of rapid methodologies capable of high throughput and broad application. However, constraints on the biochemical and biophysical processes that govern the sensitivity and specificity of many state of the art tests must be overcome before advances in real-time detection can be made. Currently, the technology for doing so is rudimentary at best, works only in pure solutions, and is generally not cost-effective. Testing is therefore generally completed only after-the-fact and monitoring of already packaged, sterilized food results in the recall of entire batches from the shelves.

Even though improvements in real-time detection technologies are not immediately forthcoming, applicant has realized that certain other forms of testing, together with the predictive power achievable with computational analysis of the test results, may achieve significant advances over the currently available tests and test methodologies.

SUMMARY OF INVENTION

One or more of the foregoing ends are achieved in accordance with the present invention by a system that employs a multispecies DNA microarray to test for presence or amount of a plurality of organisms, their metabolites or characteristic sequences. A prepared sample is applied to an array of predefined probes to detect a multispecies distribution, and a data processing module reads the array output. The output distribution is stored, with process parameters, history or other data about the sample, in a database. Preferably the module or the system further includes an informatics module that processes the array data, by look-up or correlation, to produce information of diverse types, which may relate to a sensible property such as smell, texture or taste; to processing conditions, quality or source of a component or ingredient; or to potential pathogenicity or other factor. The factors may be stored as extrinsic parameters, or developed as derived correlations, or both. In general, the system of the present invention may be seen as combining a number of recent advances in methodology for high throughput genetic testing and informatics systems to provide a new food testing procedure and equipment, which are configured such that a single test provides quantitative and qualitative information about the population distribution of microbial species in the tested sample or food product.

The method constitutes a rapid and sensitive testing procedure, and provides a volume and utility of information that add significant value to microbial testing extending far beyond the simple and conventional testing for the presence or absence of a pathogenic microorganism. The value-added parameters may include correlations between microbial profiles and characteristics such as ingredient quality, flavor potential, or the likelihood of carrying undetectable or otherwise difficult-to-detect organisms. The system itself readily produces new correlations of this type which may then be exploited for correcting process history or conditions. The information acquisition and processing module operates on the database to allow its utilization and mining, and provides a mechanism for specialization of the data to specific food products or other microbial environments, as well as to the incorporation or development of company or trade secrets. Thus, the system upgrades product testing methodology and revolutionizes thinking about food testing.

As noted above the invention employs multispecies test arrays and a data recording system, preferably with a data mining informatics system. The multispecies array is a test array in some respects similar to the arrays employed in high throughput genetic testing to sequence or identify genetic material, and in accordance with the invention, it is configured to detect specific genetic material of plural species or strains of organisms. The informatics system processes information on the distribution of target species detected by the array, and preferably their relative abundance to identify one or more parameters of food pathogenicity, quality, or correlated processing conditions or control parameters of interest. The overall operation may be implemented in an integrated and automated system, and may be optimized for each intended area of application by appropriately predefining sets of target DNA sequences that are diagnostic for sampled organisms, and identifying representative population profiles or associated processing conditions. In addition to such testing systems, the scope of the invention includes a testing service, which may, for example, utilize a database derived from many sources that includes output records for many different types of species, and operates to identify a range of potential organisms and/or processing parameters from the database of output records which may lie outside the conventionally known parameters of the process being studied.

In general, applicant contemplates a system wherein a multispecies array provides a simple test of a food sample that in one processing sequence provides information on the presence and/or quantity of organisms or identifying products thereof. While a basic system involves sampling, preparing the sample, and then labeling target products and detecting the labeled products with a test array, greater sensitivity may be obtained by an optional process step of culture amplification before nucleic acid extraction, PCR amplification, labeling of targets and hybridization to a suitably designed probe matrix array. The array is read by fluorescence detection and image analysis, and systems may be assembled from a number of off the shelf components, together with a set of easily made DNA probes, assays or markers that are specific to the organisms or materials of interest.

BRIEF DESCRIPTION OF THE DRAWINGS

These and other features of the invention will be understood from the description herein, taken together with figures illustrating representative embodiments and features of the invention, wherein:

FIG. 2 (Panels A&B) illustrates different PCR approaches useful in the practice of the invention;

DETAILED DESCRIPTION

In contrast to traditional methodologies that test for a single organism or group of organisms at a time, the present invention tests a sample to provide an output distribution representing a microbial population in the sample. The sample will be discussed in detail and illustrated for a food sample below.

A basic embodiment of the invention combines highly specific DNA probes capable of identifying many species, e.g., tens or hundreds of different microorganisms, into a single testing matrix, and each specific probe is located at a determined address or position of the matrix. The matrix, which is herein termed a multispecies array, allows the entire microbial flora present in a food sample to be evaluated and monitored. As described below, the process of testing food samples with the multispecies array may require a 12–24 hour period to complete the test, but its output provides a multidimensional distribution with added predictive power that outweighs its lack of real-time performance. The advantages include increased sensitivity, enhanced product safety, enhanced ability to understand and predict shelf-life, and an increased ability to predict the effects of ingredients, formulations, and processing on the properties of the product. By using multispecies arrays and creating a database of results, one not only identifies contaminated samples, but also sets out or measures a full set of parameters for understanding how microbial populations in food are effected by processing and formulation parameters. Because the makeup of the microbial flora can dramatically influence shelf-life and organoleptic properties, multispecies arrays can also provide value added information regarding the effect of specific populations on quality and shelf life parameters of a given food. The invention is equally applicable to environmental and workplace testing, where multiple species depend in complex ways on surrounding parameters.

The Probe Arrays

The invention employs a specially-constructed probe array to test for microbial gene sequences or products. Probe arrays, perhaps one of the greatest revolutions in biological methods since the development of the Polymerase Chain Reaction (PCR) methodology, rely upon the ability to fabricate small surfaces containing many different DNA probes at specific addresses so that the detection of labeled material at those addresses indicates the presence of the specific materials to which the probes are directed in the original material. This has provided enabling technology for high-throughput genetic testing, because rather than detecting a single gene or a group of genes, DNA probe arrays can be fabricated to simultaneously profile vast portions of the genome of an organism. Thus, the expression pattern of each gene of a given organism can be simultaneously monitored under different growth conditions. The present invention applies this approach not to drug discovery and understanding of diseases, but to monitoring microbial populations in a sample, illustratively food. The method and system of the invention may also be applied to clinical, industrial, epidemiological and environmental samples. Rather than an array of probes from the genome of a single species, the multispecies testing arrays of the invention have probes arranged at addresses specific for many different microbial species, and may include different strains and specific gene sequences within species to be found in the sample. With an array of one thousand probes, for example, one can test for one hundred different organisms and employ ten different probes for each organism. Thus, detection and quantification of any single organism may be based on multiple data points. This feature offers the prospect of detection of the presence of an organism in cases where the detection threshold of a conventional assay is too high to permit effective detection or quantification. Thus, the array provides greater information about the tested sample.

As described further below, applicant contemplates that the multispecies arrays of the present invention are preferably sampled by an automated array reader, and their data outputs are preferably mined, correlated and developed into new, multiparameter tests for diverse measures of food quality and process conditions. The amount and usefulness of information obtained from testing multispecies arrays is effectively limited only by the creativeness of the array design and by the "data-mining" power of the software which analyzes the data. In the context of food samples, applicant contemplates fabrication of arrays having probes specific for all known bacterial pathogens that could be carried in the intended food sample, as well as spoilage and commensal organisms. Such an array would therefore enable evaluation in a single test of not only the safety of a product, but also parameters that contribute to its shelf-life and organoleptic properties.

Value-Added with Test Results from Probe Arrays

The traditional approach of food testing has been to examine the sample for the presence of a single species of pathogenic microorganism or group of indicator organisms such as coliform bacteria. Even state of the art testing based on genetic identification is designed to detect a single target gene from a single species or closely-related groups of microorganisms. However, by designing a suitable multispecies testing array, and by configuring an informatics system to present data from the array, the invention effectively screens entire microbial communities in a single test. By providing a correlation module to correlate information about the population distribution of microorganisms with any factor or other extrinsic data, the distribution output may be extended to yield other useful information. Such extrinsic factors may be present as fields or associated records in the database, indicating, for example, a processing condition, food component source, or simply the array output (i.e., test results of multiple organisms in the array).

Several example applications of correlating output distribution include the detection of dangerous conditions by correlation between new indicator organisms and undetectable pathogens; detection of quality-related conditions, for example, by correlation between particular species and the shelf-life of a product or its organoleptic properties; and correlation between specific ingredients (e.g., the specific suppliers of an ingredient or formulations of ingredients in a product) and the presence or growth of problematic microorganisms. These correlations may be determined automatically, i.e., discovered by data mining programs that automatically access, update, and correlate information in a database. The database may be generated from array output distributions for the tested samples, together with extrinsic information such as conventional records of batch lot numbers, ingredient invoices, product returns and later-reported or later-detected contaminants. The correlations so derived, and the database and testing criteria that are established in this manner in a product processing line, thus form a database that, over time, may constitute a valuable proprietary trade secret.

By way of example, one value-added piece of information obtainable from the invention's multispecies array testing methodology may be the finding that the texture of a particular food product becomes slimy due to the production of extracellular slime by a species of spoilage bacteria such as *Alcaligenes eutrophus*. The present invention allows such an observation to be carried further. By maintaining an historical database of test results with other observed parameters, one may then, using stored testing array output distributions, discover preconditions and causative factors. For example, database correlations may show that *A. eutrophus* is commonly present, but that it only synthesizes the slime when growing in the same microenvironment as certain species of *Pseudomonas*. Observation of this correlation would lead to a conclusion that *A. eutrophus* presents a practical problem when Pseudomonads are also present in high numbers. Several such examples of extracellular compounds or byproducts from one species of microorganism impacting the physiology of a second species have been reported in scattered microbiological studies in the prior art. By adopting a multispecies array testing methodology, the discovery of further relationships of this type may be automated, and follow naturally from correlation of output distribution test data from the multispecies array testing of food products.

A second example of the power of applying data mining to the multispecies array distribution records is the identification of microbial profiles among ingredients that are indicators of potential problems with subtle organoleptic properties of the food. In this instance, data from testing ingredients used in production of processed vacuum-packaged meat products may demonstrate, for example, that an off-flavor is consistently reported for batches when the recorded distributions for those batches show that certain species of the genus *Carnobacterium* are present in the ingredients. Further mining would then allow correlation of test results with the source of the tested foods to allow discovery of which suppliers provided ingredients containing those specific species or strains of *Carnobacterium*, or which processing conditions permit its growth, and therefore may be more likely to produce off flavor.

In addition to identifying new correlations between microbial populations and product properties, the multispecies arrays by repeatedly determining the spectrum of species in a fixed food, process or environment also enable the determination of new correlations between detectable species that can then be used as highly-specific indicator organisms. For example, while coliform bacteria have been used classically as indicator organisms, their presence is not necessarily a sufficient indicator of fecal contamination, since many coliform species can also be found naturally on plant material. This makes their potential as an indicator for fecal contamination on raw ingredients less useful. With the use of a multispecies array and data-mining informatics, software can automatically record the species present in food samples and determine which specific organisms are associated with pathogens. Thus, the array miner may "discover" that when the specific coliform profile contains primarily species of Enterobacter, there is poor correlation with the presence of enteric pathogens such *Salmonella enterica* or *Shigella* species. On the other hand, the informatics software might also determine, by "discovering" a correlation, that when the coliform bacterium *Klebsiella oxytoca* is present along with *Citrobacter fruendi*, there is a much higher probability that the coliform bacteria came from a source where enteric pathogens could be present. The invention utilizes this type of multi-component correlation to implement new screening or testing methodologies. With such an indicator or test criterion, then, when a testing array scores positive for *K. oxytoca* and *C. fruendi*, one pulls the product aside and tests more thoroughly for the presence of low levels of *Salmonella* and other enteric pathogens. Furthermore, new arrays may then be fabricated to detect the specific species required for the newly-identified screening tests.

Although each of the above examples is hypothetical, they illustrate biologically reasonable approximations of the type of information present in array test data, which is simply and automatically derived by data mining, and they illustrate the range of substantive knowledge and new testing protocols of the invention. These examples specifically illustrate the value-added component that multispecies arrays and data mining provide, as compared to a conventional test for the simple presence or absence of specific pathogens. Thus, the key elements of the approach are the configuration and fabrication of the testing array, the data mining method, and its extensions to provide specificity, depth, and proprietary databases of test data, correlations and derived knowledge.

System Operation

Figure 1:
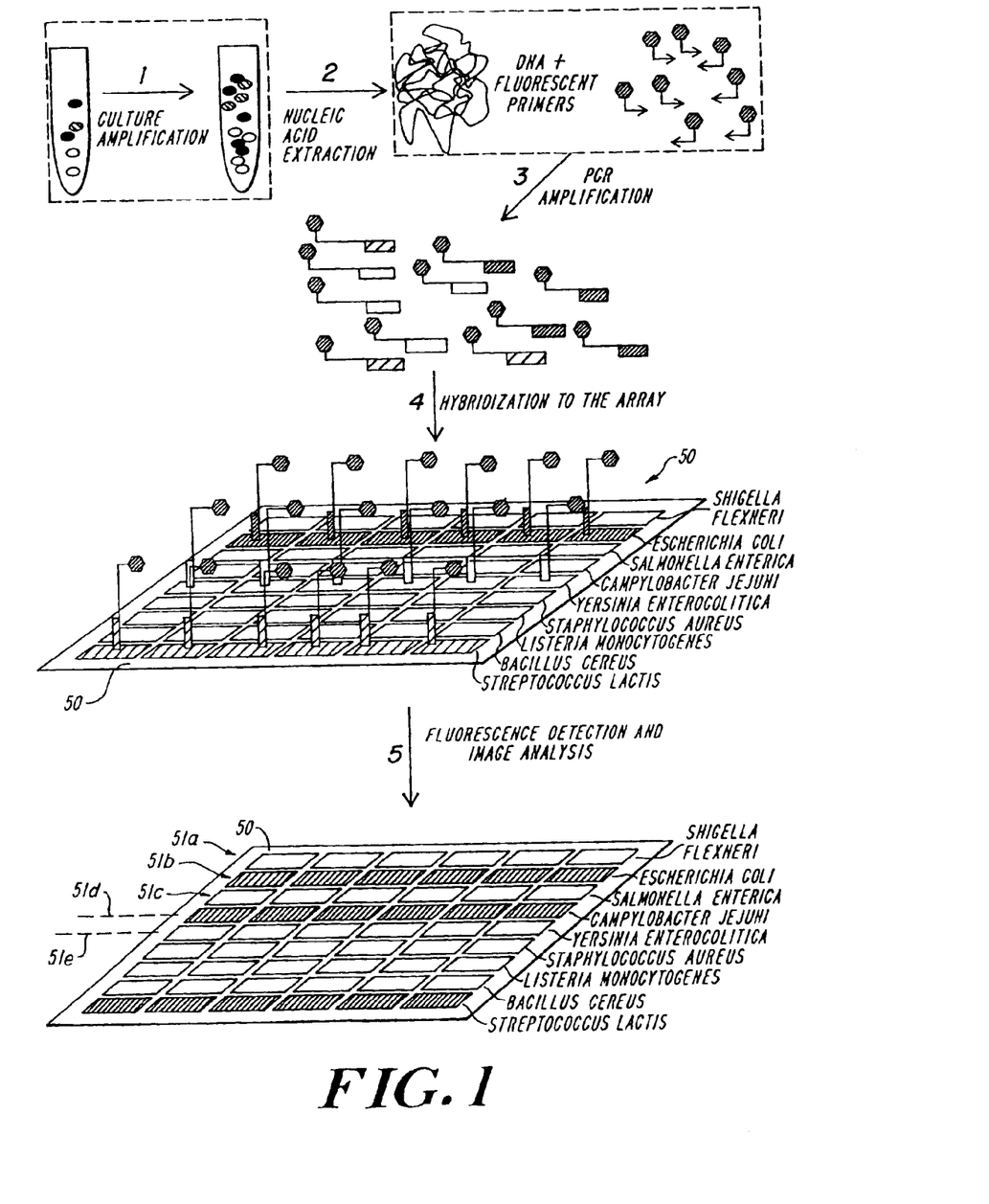
FIG. 1 illustrates a multispecies test array useful in the practice of the invention.

An overview of steps of the present invention is illustrated in FIG. 1 and is described below.

The multispecies array testing system of the present invention is preferably implemented as a completely automated system, with high-throughput potential and low cost per sample. A basic embodiment of the system prepares a food sample and tests for a palette or distribution of organisms or genetic material characteristic of the set of organisms by labeling material prepared from this sample and reading the labeled material in each of a plurality of wells or positions of an array. The process may also be tailored to detect organisms with higher sensitivity by first culturing the sample with a culture medium cocktail to simultaneously multiply several different cell populations before extracting DNA for array testing.

Typically, the entire testing procedure, with the culture amplification step, may take approximately 8–12 hours per sample and include five steps: i.) a culture step (e.g., 6–8 hours) designed to increase a subgroup of target populations of microorganisms; ii.) a sample preparation step which may include extraction and concentration of nucleic acid from the cultured organisms; iii.) a target amplification and labeling step in which the polymerase chain-reaction (PCR, is used to amplify a plurality of different targets and label the amplification products with fluorescent compounds; iv.) a hybridization step in which the labeled amplification products are allowed to hydrogen bond to their respective target probes on the multispecies array; and v.) a detection step in which the fluorescence intensity of each probe address on the multispecies array is detected. Preferably the process is automated, although it may also be performed by manual culturing and sample preparation.

One embodiment of a process in accordance with the present invention using a multispecies array is shown in FIG. 1 for testing a food sample. In a first Step 1, the food sample is inoculated into a culture medium and incubated for a sufficient time to permit multiplication of the cells. Different species of microorganisms are represented by different shading in FIG. 1. The Figure illustrates the process schematically with a single test tube as a culture vessel, and preferably the culture process is designed to simultaneously culture all, or many, of the target species simultaneously. However, the sample may also be divided and placed in two or more vessels that present different culture conditions, so that each vessel is effective to simultaneously culture a subgroup of the targeted number of species.

In the second step 2, nucleic acids are extracted (as indicated by the squiggly line) and are mixed with PCR reagents, preferably including fluorescently-labeled PCR primers. In the Figure, arrows with black stars represent the fluorochrome.

In the third stage 3, enzymatic amplification by the polymerase chain reaction (PCR) is carried out with labeled probes to increase the number of segments of the genomes from each of the target organisms, with each amplified segment containing a fluorescent label. In the Figure, target genes amplified from the microorganisms present in the original food sample are shaded differently to indicate different species from which they originated. In a variation of this step, amplification may be performed with unlabeled probes, and a chromophore or other label is added during the amplification or subsequently. For example, to effect subsequent labeling, biotinylated probes may be used, thus retaining the PCR products on a column, with a subsequent step of eluting the amplified biotinylated strands onto the array, and applying labeled antibodies to the immobilized material. Another post-synthetic labeling method may include chemical cross linking of fluorochromes onto different moieties of the amplified DNA chains.

Continuing with a description of FIG. 1, after the described amplification/labeling of step 4, the fluorescently-labeled PCR amplification products are allowed to form specific hydrogen bonds with complementary sequences located on a probe array 50. The array 50 is constructed such that each individual address, represented in the Figure by a rectangle on the probe array, contains a different gene probe, and such that within a given row 51a, 51b . . . of the array, all rectangles or sites contain probes specific for gene sequences of a single species or strain. Thus, the fluorescently-labeled PCR amplification products will form hydrogen bonds specifically with the complementary probe from the row and column corresponding to the species and gene respectively from which it originated.

Finally, in step 5, fluorescence detection and image analysis identify the addresses on the multispecies array which fluoresce and, in some embodiments, may also quantify the degree of detected fluorescence. The probe addresses testing positive are indicated in black in FIG. 1.

Implementation of the foregoing steps in done as follows.
Culture or Other Amplification of Target Organisms Because food matrix compounds can have profound inhibitory effects on PCR amplification, bacterial cells are separated from the food matrix before performing PCR. Systems of the invention may employ two basic approaches to achieve this. The first approach separates of the target cells or their nucleic acids from the food matrix, for example using microfluidics devices. Systems employing microfluidic sampling and preparation may be optimized to provide favorable performance in terms of real-time assays or speedy performance. In this approach, a microfluidics system is programmed and prepared with the necessary reagents for automated sampling and purification of microorganisms and their nucleic acids from the sample. In the second approach, the cells are multiplied by elongation and division in culture, so they increase logarithmically over time. Most foodborne organisms of interest have doubling times ranging from about thirty minutes to one hour under favorable conditions. Thus, a six hour culture step would allow six to twelve doublings of the population. Because of varying nutritional requirements of different species, differences in growth rates (causing faster growing cells to overtake the culture), and the presence of process-injured cells, it may in some cases be difficult to devise a single medium that permits efficient growth of all target organisms. In that case, one may provide a few different types of media to enrich the populations of different species or groups of species.
Nucleic Acid Extraction After collection of the microbial cells from the food sample and lysis of the cells to release the nucleic acids, the nucleic acids are concentrated by precipitation or by adsorption to a solid matrix such as hydroxyl apatite, glass, diatomaceous earth, or plastic, and PCR amplification (described below) is performed on the immobilized genetic material. The extraction step may be performed manually in a prototype by simply adding chaotropic agents to the culture, followed by pouring the mixture through a small sample preparation column or cartridge containing an adsorption matrix. The column cartridge may then be washed and placed into a device for PCR amplification. Preferably, the system of the invention employs a special cartridge configured for automated implementation of several subsequent steps. In this aspect of the invention, the culture or food sample is poured into a cartridge that fits into a fluidics system having automated fluidics pumps that then operate to perform cell lysis, nucleic acid extraction, washing, and PCR amplification within the cartridge. There are currently several prototype fluidics systems on the market and in Federal laboratories that function on the meso-fluidics (milliliter volumes), micro-fluidics (microliter volumes) and nano-fluidics (nanoliter volumes) scales. For food testing, applicant contemplates an automated system of the invention as a meso- or micro-fluidics system with an integrated system controller that is set or programmable to pump the appropriate sequence of solutions through the cartridge. An existing commercial sequence labeling system may be augmented to add such PCR capability by providing a thermal jacket or other heating mechanism around the cartridge, with additional controller functions to provide thermal cycling to implement PCR incubations for amplification.
PCR Amplification and Fluorescent Labeling Implementation of this step involves selection and optimization so as to enhance the sensitivity and specificity of the test. The PCR amplification step consists of using short oligonucleotide primers as substrates for enzymatic amplification of different target segments of the genomes of organisms present in the culture. Probes corresponding to these target segments are also provided on the array 50. In the embodiment illustrated in FIG. 1, each PCR primer is labeled with a fluorochrome. After amplification by the PCR process, the fluorescent amplification products contain enhanced levels of the target sequences that are complementary to probes on the multispecies array which are specific to the strains or species of interest for which the array has been configured.

Figure 2A:
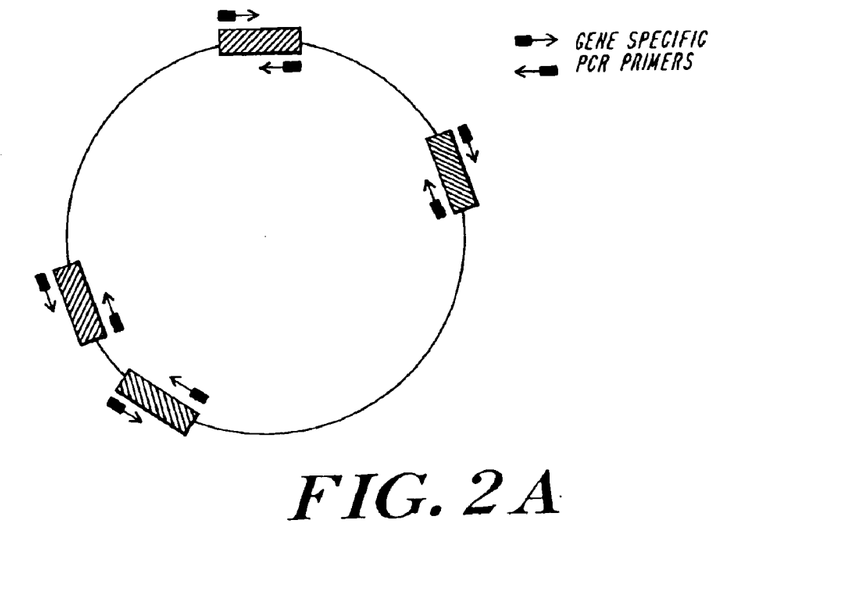
Figure 2B:
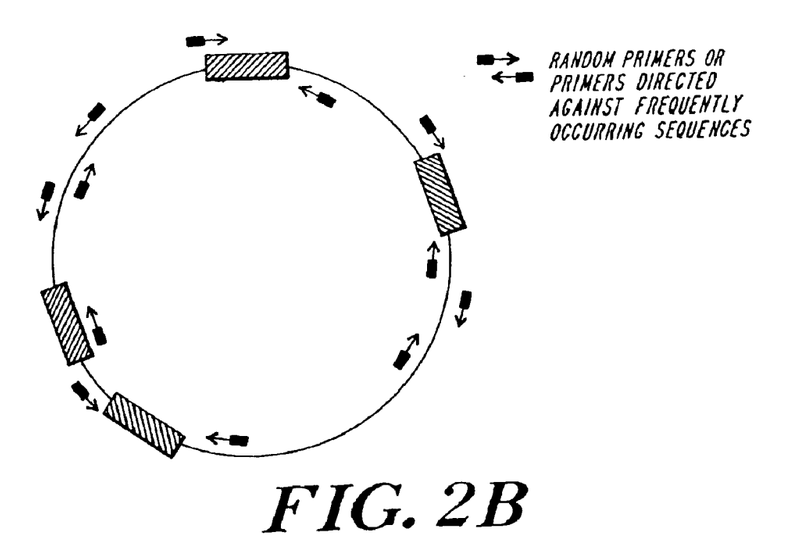

Implementing optimization of this amplification and labeling step is carried out by selecting and evaluating fluorescent primer combinations so as to identify those which most effectively amplify the desired target sequences. Applicant contemplates general approaches that may be used: amplification of the specific target sequences, or amplification of a variety of segments of the chromosome including those which are complementary to the target probes. As illustrated in FIG. 2, this involves making or selecting sets of gene-specific primers that are capable of specifically directing enzymatic amplification of each target as shown in panel A of FIG. 2, or selecting sets of primers that direct amplification of multiple segments of the genome, only some of which contain gene sequences that are complementary to probe addresses on the multispecies array, as shown in panel B. Yet a third approach is to use short sequences that are common to sets of target genes as sites for primers. Each of these approaches may be used. The first method offers the prospect of enhanced specificity or sensitivity. As noted above, the invention also contemplates methods wherein the DNA is fluorescently labeled during or after amplification; this may allow optimization of the amplification step with fewer constraints, or permit a greater signal level to be achieved to further optimize an array and processing system.

FIG. 2 illustrates the two different methods for PCR amplification and fluorescent-labeling of the products. Enzymatic amplification by the PCR process occurs between the PCR primers, shown as small rectangles with arrows, that are directed to particular positions in the chromosome, which is depicted as a large circle. Portions of the chromosome having gene segments that are targeted by the multispecies array are indicated by large shaded rectangles. For simplification, only one chromosome from only a single species is represented. In panel A of FIG. 2, each specific target gene is amplified by a highly specific set of primers that direct enzymatic amplification only of segments from the genome that contain genes being targeted by the multispecies array. In Panel B, the same target genes are amplified; however relatively non-specific PCR primers are used, and they amplify several segments of the genome, which include the target genes but also include other segments that are not targeted.

The determination whether a system of the invention uses PCR primers that are fluorescently labeled, or else incorporates fluorescent labels into DNA chains produced during the PCR amplification process (either concurrently with or following DNA synthesis) may depend on factors that vary with the particular combination of species targeted with the array. One advantage of using labeled primers is that fluorescent primers can easily be synthesized and purified, and thus will not have to be optimized. On the other hand, the use of a labeled primer results in incorporation of only a single molecule of the fluorochrome per DNA chain, whereas incorporating fluorescent bases into the growing or completed DNA chains during or after PCR amplification can provide DNA chains with multiple molecules of fluorochrome per chain, thus increasing the signal level and the sensitivity of detection substantially, e.g., as much as ten-fold. However, one cannot rely blindly on incorporation of flourescent bases during PCR to raise sensitivity, because the thermostable polymerases have a low affinity for most labeled base analogs and thus, the labeling process may not be as efficient as one would desire. Thus, applicant further contemplates embodiments wherein the amplified nucleic acids are chemically labeled after amplification to optimize the process for a given array with specifically-targeted organisms.

The last issue to consider in regards to fluorescent labeling is which fluorochromes to use. The fluorochromes currently available can be divided roughly into two categories: those that fluoresce in the visible wavelengths of the spectrum and those that fluoresce in the near-infrared (NIR) region. The type of fluorochrome that is used will dictate the type of detection system that is employed to read the array. The signal to noise ratio for the NIR region of the spectrum is highly favorable and can offer detection limits that cannot be achieved in the visible region. However, relatively few IR fluorochromes are currently available and, due to their size and chemical properties, these may be incorporated even more poorly than visible fluorochromes during PCR. Presently, although prototype NIR array detection instruments are available for development purposes, NIR detection systems are not on the market, and the prototypes that are available detect larger spot sizes which would require a larger size testing matrix, array 50. However, the range of available probes and equipment may grow quickly, and applicant therefore contemplates selecting or developing suitable fluorescence labeling based on both visible and near-IR fluorochromes for prototype implementations of the system to evaluate which will provide the most efficient testing system. Thus, applicant contemplates simultaneously building or selecting appropriate materials for use in each of these labeling/detection technologies.

Probe Matrix and Array Design

The probe matrix 50 shown in FIG. 1 is laid out such that each different row contains six different probe addresses for a single organism. Each probe address contains several thousand molecules of a particular probe. Larger arrays of this type may be fabricated with hundreds of rows and columns of probe addresses. Several different methods may be employed for arraying probes onto the solid matrix. These approaches fall into two different categories: those based on synthesizing probes onto the surfaces in situ and those which involve deposition of pre-made probes onto a surface.

Methods available for depositing or spotting pre-made probes onto surfaces allow one to rely on a broad range of commercially available probes. These spotting methods fall into five different categories. These include those based on capillary action to lift and expel samples, those based on electrochemical reactions to focus charged probes to specific addresses on the testing surface, those based on ink jetting technology to spritz samples onto surfaces, those based on precision micropipetting, and the quill-based technologies. Electrochemical devices currently produce only small arrays. Current arrays of this type have a size of approximately 100 spots and thus could produce only limited distributions that would not embrace the full range of value-added potential discussed above for applying the testing array output distribution. Currently, several systems involving the use of capillary action, micropipetting, and quills are on the market. The selection of technology for an array system may take into account the advantages and disadvantages of the different array-making systems to effectively fabricate prototype or commercial embodiments of applicant's multispecies arrays, and these may differ for different sets of target organisms, or intended applications.

Because critical criteria such as compatibility with the materials or processes of a given technology may not have been explored for some of the target species or materials contemplated herein, preferably some model arrays are first fabricated by the intended user with the equipment or processes of select vendors, and evaluated to determine the most suitable system.

The array size, and provision of multiple probes per targeted organism, is an advantageous feature of the invention. With an array of one thousand addresses, one hundred different microorganisms can be targeted with ten different probes per organism. Detection of any one of the organisms being evaluated would therefore be based on ten datapoints. Having multiple datapoints increases the specificity and statistical reliability of the test, and allows strain-specific as well as species detection to be implemented. Moreover, it also provides several data points from which to derive quantitative information. It also allows applicant to design a single array, but to vary which organisms are tested for and which target DNA sequences from a given species are be used for detection.

The species one tests for may differ among different types of food matrices, but one general approach for a basic embodiment of the invention is to have addresses for coliform organisms and other enteric bacteria, and addresses for known foodborne pathogens, spoilage organisms, and commensal flora. Genes that can provide a molecular signature of each species or strain are preferably used. This may include groups of genes that are found among each of the species, but with probes designed to detect regions of the genes that are specific to each species. A second group of genes to be targeted are genes that provide specific signatures of each species, such as virulence genes for pathogens, and genes encoding degradative enzymes for spoilage organisms. Genes that encode enzymes of specialized biochemical pathways may also be used as diagnostic markers or indications for each different species. In addition, the probe may also be configured to detect gene sequences for which the function is not known, but which amplify well and are highly specific to the targeted species.

In addition to discrimination at the species level, specific probes may be used for discriminating microorganisms at the sub-species level. For example, genes encoding specific virulence factors could be used to discriminate different populations of pathogenic strains of *E. coli* from non-pathogenic strains that might normally reside in samples of some types of food. As another example, genes specific for biochemical pathways found among sub-species of fermentation organisms may be used to determine which species of lactic acid bacteria were present in raw vegetables that were intended for a fermentation process.

Thus, applicant contemplates that multispecies arrays of the invention may be generally directed to a palette of generally relevant species, or be tailored to a more specific food application and directed to the different microbial species and the different types of target genes that are relevant to that application. Thus, the invention may employ product-specific arrays, as well as generic arrays that are useful for a wide variety of samples.

Fluorescence Detection and Image Analysis

After the fluorescently-labeled PCR amplification products from the original microbial population have been hybridized to their respective addresses on the multispecies array, the hybridization events are detected by image analysis of the pattern of fluorescence. As illustrated in FIG. 1, the addresses where fluorescence occurs in the array then provide a signature of each species present in the sample, and the collection of fluorescent addresses provides a population distribution of the species present in the samples. This is read out by an image analysis system which may apply detection based on fluorescence signals emitted in the visible or Near-IR range, or a customized reader may be built to detect both spectral regions. Which region of the spectrum is chosen may be based on the behavior (sensitivity and specificity) of the fluorochromes that are used to label the PCR amplification products. As noted above, initially applicant contemplates the use of commercially available label material with fluorescence in the visible band.

In addition to simply creating an image of the fluorescence intensity of the addresses on the array, sampling software converts the output to a user-friendly format, such as a simple bar graph representation of the fluorescence intensity of the species associated with array addresses, which may be normalized relative to a baseline control. Such an output allows an educated analyst to evaluate the entire array for both presence/absence and relative abundance of target organisms in the original sample based on the intensity of the fluorescence. The software may also quantify and compare the test readings internally, and provide an output highlighting which organisms are present, their estimated abundance and explanatory notes or highlights regarding warning thresholds, unusual or out-of-limit results or the like.

Data Mining and Correlation

In accordance with a further aspect of the invention, the processor is configured to mine, correlate, and screen data so as to detect information or develop detailed knowledge applicable to the species, to the processing and to the food products being tested. Thus, in a mining mode, for example, the user may compare the different parameters of the sample with similar samples in the database to determine where it lies in larger context or world of possible or desired conditions or results. This mode preferably employs a relational database that links the microbial population landscape to other parameters of the food sample. Thus, the user can evaluate the sample in terms of the average distributions of species relative to the database. Action levels may then be set based on deviant distributions rather than on arbitrary values or on a regulatory threshold for a single species or class.

One method for conducting such an analysis is by superimposition of the population profile detected by the array onto a landscape of parameters or sentinel measurements. These parameters may include data parameters provided by non-bacteriological detectors of process conditions, such as pH, starch or sugar content, or a measure of volatile components. Comparison of the sample profile on this landscape with the normal distribution is then applied to provide predictive information on the quality of the tested sample.

Figure 3:
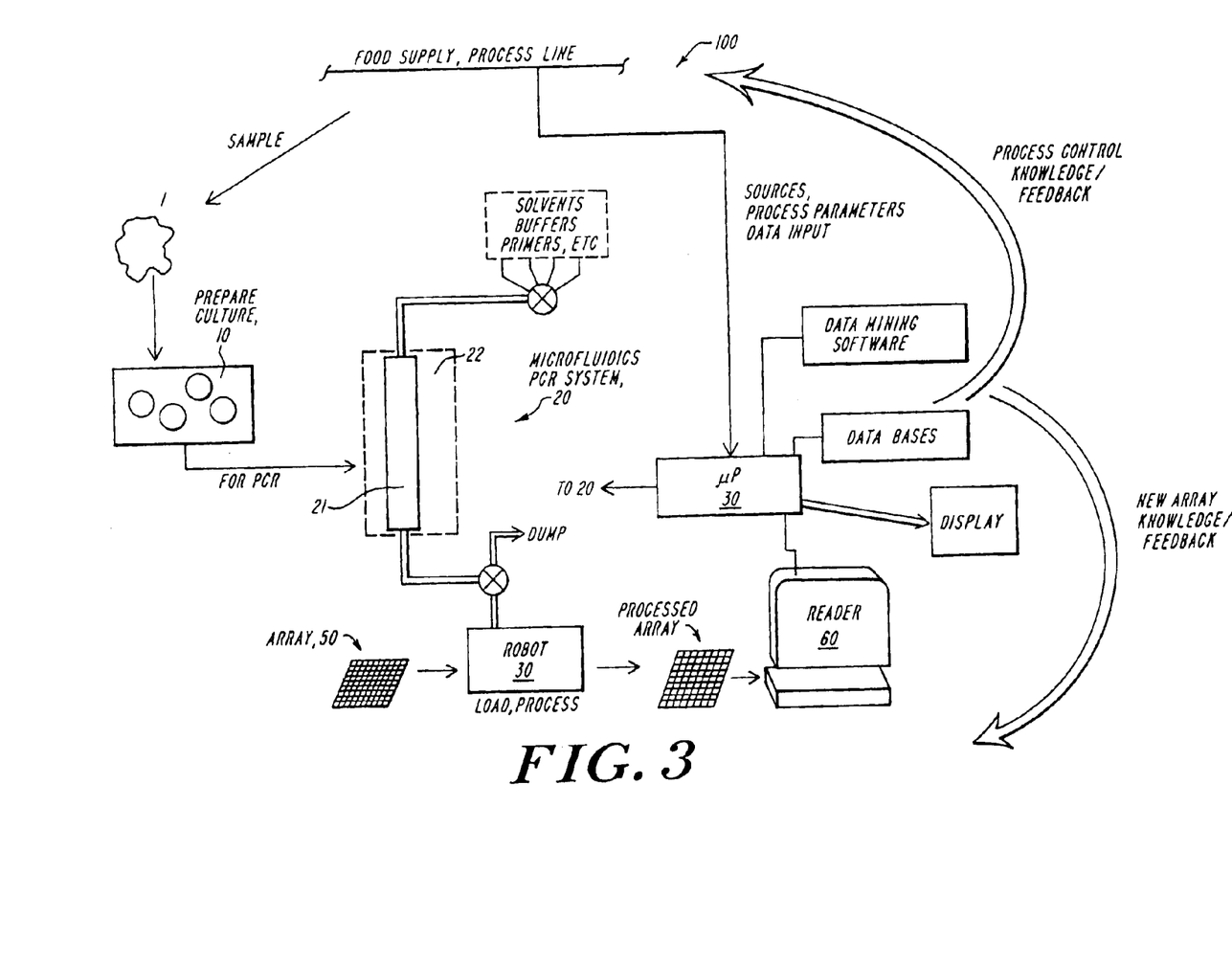
FIG. 3 shows a system of the present invention.

Thus, as shown in FIG. 3, the processor 30 may receive keyboard-entered or bar-coded data or direct input of data from parameter sensors in the process line to indicate the various processing parameters for the lot being tested. Inputs may also be provided from other sources, such as keyboard or bar code entry of data from invoices and inventory slips, to indicate the source or age of each ingredient, and any special conditions such as early or late harvest, dry or wet growth season or other factors that may either aid in understanding the array reader distribution test result, or may be desirable to monitor or change in view of the array results. Thus, for example, if one source of raw produce is found to supply produce with an unusually high level of an adverse species, the correlation processor may identify this condition with the source and allow appropriate actions to be taken.

Similarly, extrinsic data on taste, color or other quality checks may be entered in the database, and correlated with any of the array results or data fields to provide predictive knowledge for process control, or to guide the addition of new species to the test array.

System Implementation

For building initial multispecies arrays of the present invention, two fundamental approaches may be used. One can simply design the arrays and have them fabricated commercially by a vendor of such services. Alternatively, the arrays may be produced within the research or food-processing entity itself. Although the former approach may seem advantageous, convenient and inexpensive during the initial stages of assay implementation, applicant's invention contemplates on ongoing process of array development or evolution, and it is preferred in the long run to have an array maker available through the food processing corporation or other entity that is actively controlling the preparation and processing steps. This facilitates making alterations to the arrays to address transient or evolving concerns, and simplifies optimization and evolution of the array and the array-based testing methods. It also allows the processor to exercise enhanced quality control, and will conveniently allow production of the arrays to be coordinated with processing and increased when it is desired to increase the output potential of a process or of the array maker. Since the information-mining operation of the system is expected to result in continual creation of new tests or optimizations, in-house array making will greatly speed up the incorporation or evaluation of ongoing developments. The actual array fabrication process may employ any of the several array maker types currently on the market. In general, the range of utility of a given array-making device, its component costs and the operating times required for its various steps as well as the range of adjustable parameters may vary widely and thus, affect its utility for the purposes described herein. Thus, in deciding on which array fabrication machine to employ, and unless or until the specific assays dictate one technology, the invention may employ any system that offers flexibility and economy to perform a range of preparation, amplification and labeling tasks outlined above.

Probe Configuration

The initial selection of species and probes for a test array is straightforward. This may be done by selecting an appropriate number of target organisms or species that are already known to be of interest, and then searching a database such as GenBank to obtain a list of gene sequences that have been identified for each of the species. The gene sequences may be cross-checked to identify which ones are specific to the organism, or ones which are common to several, or a class of organisms may be used. Among the gene sequences so identified, one may select particular ones that encode a toxin, or are important for virulence, or are otherwise associated with a known and important trait such as a biosynthetic pathway. Probes are then made for the selected sequences for each species to fill in the array and to carry out the full processes of amplification, labeling and array detection.

For example, on a model array, the applicant has fabricated several classes of genes from different organisms that singly and collectively are diagnostic of those organisms. Toxin-encoding genes that have been fabricated onto the array are the hemolysin BL (hblA, hblB) and enterotoxin B (entB) genes from *Bacillis cereus*, Listeriolysin O (hlyA) gene from *Listeria monocytogenes*, enterohemolysin (ehxA) and shiga toxin (stxA2) from genes *E. coli* O157:H7, enterotoxins A, G, D, I, (entA, entG, entD, entI) and toxic shock toxin (tsst-1) genes from *Staphylococcus aureus*, and the shiga toxin (stxA) and vacuole-forming toxin (vacB) genes from *Shigella dysenteriae*. Other genes that participate in various aspects of virulence or pathogenicity that have been fabricated onto the array include ipa-P60, ltrA, mpl, inlB, inlA, plcA, and plcB from *Listeria monocytogenes*, yopD, yopB, yopH, yopE, virF, yopN, yopP and yopM from *Yersinia enerocolotica*, sarA, from *Staphylococcus aureus*, icsB, ipaC, ipaB, and virF from *shigella dysenteriae*, sopE, pagC, invJ, spiA, prgK, and invH from *Salmonella enterica*, and hlyA, toxB, espP, eaeA, etpC, and escT from *E. coli* O157:H7. Other genes on the array comprise a broad category of genes encoding components of specific biochemical pathways that are diagnostic of particular organisms. Sporulation genes are diagnostic of spore forming species such as *Bacillus subtilis* and include the spoIIGA, sigB, spoOA and spoIIAA that have been fabricated onto the array. Genes encoding unique biochemical pathways have also been fabricated onto the array including the beta-glucuronidase (uidA) and beta-galactosidase (lacZ) genes from *E. coli*. Lastly, genes that encode common functions but have unique structures for diagnostic purposes have also been included on the array. These include the dacF gene of *Bacillus subtilis* that participate in cell wall synthesis, the pglA, pglD, pglF, and pglB genes of *Campylobacter jejuni* that are involved in protein glycosylation (and potentially virulence), the cipA gene encoding a phosphatase and flaB gene encoding the flagellin subunits of the flagellum of *Campylobacter jejuni*, the aspartyl-tRNA and threonyl-tRNA encoding genes (asp-tRNA and thr-tRNA), the ribosomal RNA subunit gene (23SrRNA), the secondary sigma subunit sigma B encoding gene (rpoS), and the glucose dehydrogenase gene (gdH) of *E. coli*, the nuclease encoding gene of *Staphylococcus aureus*, and fir gene of *Shigella dysenteriae* that is involved in iron uptake, and the traJ and the traK genes encoding plasmid transfer functions in *Salmonella enterica*.

Initially, the primary genes of interest will be those which are important for virulence in specific species. However, once a database of test results and related process or ingredient histories is established second-generation research or detection probes may be fabricated to extend the range of useful results. The process for forming such second-generation arrays will be somewhat different. For example, one may get a listing of all gene sequences in GenBank for a particular organism, then cross check the sequences to determine which are unique to the subject species or strain. As before, one designs appropriate probes for amplifying and detecting the characteristic sequences, and the resulting array and process are then used under a range of variation to quickly determine the specific sequences that provide greatest sensitivity, provide compatibility with a PCR cocktail, and other properties for optimizing array configuration. The sequences need not code for virulence or, indeed, need not have any recognized function. The ability to use any sequences listed in GenBank for the target organism allows one a large choice of suitable gene sequences for identifying the target organism while achieving simultaneous compatibility with common processing cocktails for multiple species. Alternatively and additionally, diagnostic sequences may be identified experimentally. One approach would be through design and implementation of a single species array having addresses that represent the entire genome. This array is then probed with the entire genomes of closely related species to find addresses to which no corresponding target sequence can be found to hybridize from other species.

EXAMPLE

To examine sensitivity and specificity of a multispecies array, a model array was fabricated to detect seven different species of pathogenic microorganisms, a spoilage organism, and one indicator organism. These were the pathogens *Listeria monocytogenes, Staphylococcus aureus, Escherichia coli* O157:H7, *Shigella dysentariae Yersinia enterocolitica, Campylobacter jejuni,* and *Salmonella enterica* Var. *typhimurium*. Generic *E. coli* was taken as an indicator organism, and the selected spoilage organism was *Bacillus subtilis*. Ten diagnostic genes were chosen from each of these organisms, amplified by PCR, and the products deposited on an array on poly-L-lysine coated glass slides. Each array included duplicate addresses that contain probes for each of the target genes, and six different control addresses that contained varying amounts of DNA encoding the green fluorescent protein used for labeling, which is not known to be carried by natural populations of bacteria. Performance of the array was then examined by applying PCR amplification products from known concentrations of DNA purified from *Bacillus subtilis*, (1A-1R) *Salmonella entericia*, (8A-8R) *Listeria monocytogenes* (1S-1X, 3S-3X, 4S-4X) and *E. coli* O157:H7 (5S-5X, 6S-6X, and 8S-8X). The amplified target PCR products were labeled by incorporation of fluorochromes into the growing DNA chains during each round of enzymatic DNA polymerization during the PCR reaction. *Bacillus subtilis* and *E. coli* O157:H7 amplification products were labeled on one channel (green) while *Listeria monocytogenes* and *Salmonella entericia* were labeled on a second channel (red). The labeling method was performed on dilutions of the target DNA ranging from $10^{-2}$ to $10^{-7}$, which were calculated to represent a range of target cells from $10^6$ to $10^1$.

After chemically blocking sites on the slide surface where no probe molecules exist (i.e. between the addresses and on the edges), the labeled products from the different dilutions of target DNA were hybridized to the array overnight in Tris-sodium citrate-SDS buffer at 62° C. The slides were then washed three times in sodium citrate buffer to remove excess labeled target DNA molecules and were scanned in a commercially available scanner. The relative fluorescence intensity above background was recorded.

Figure 4:
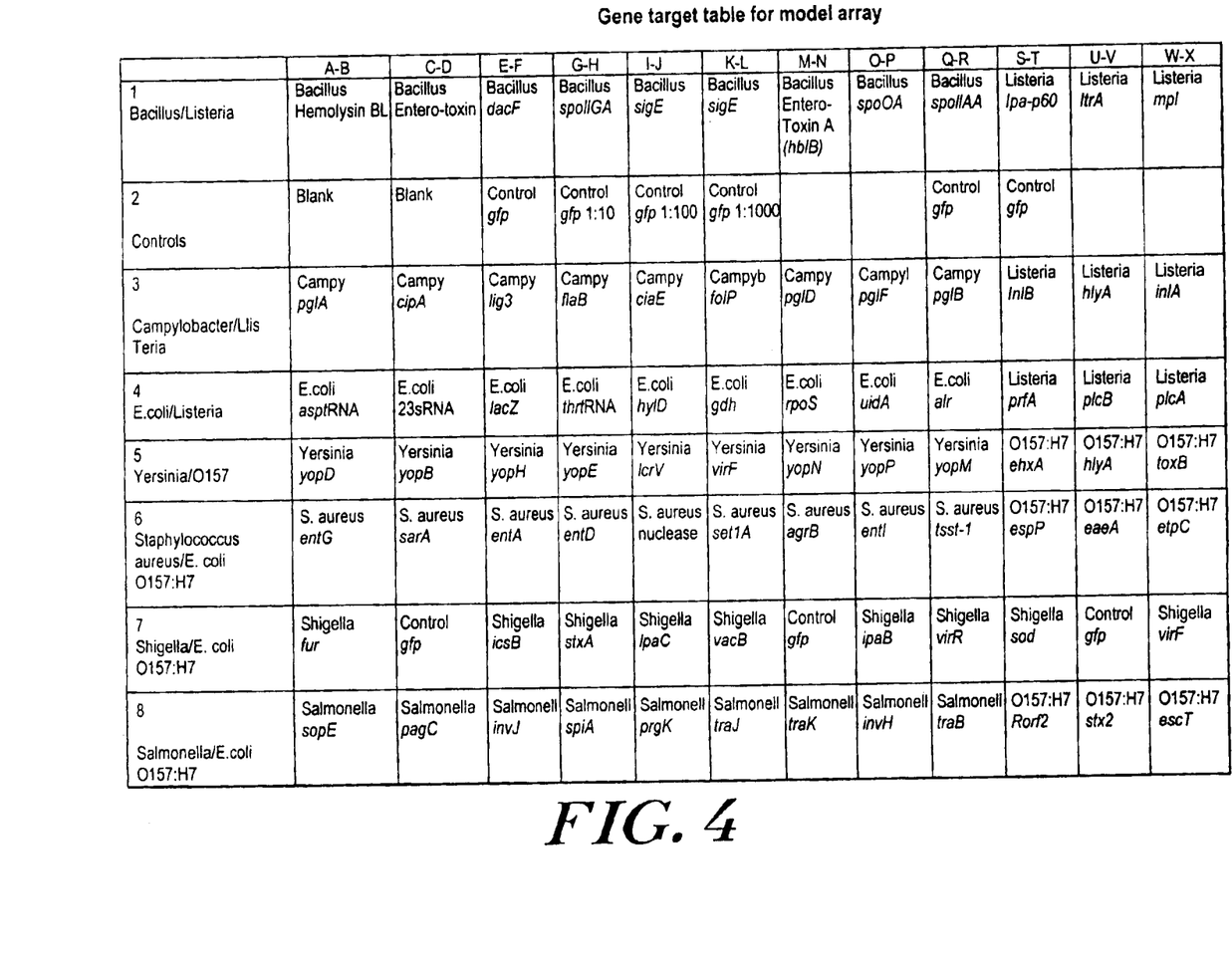
FIG. 4 illustrates layout of addresses and content in one embodiment of an array.
Figure 4A:
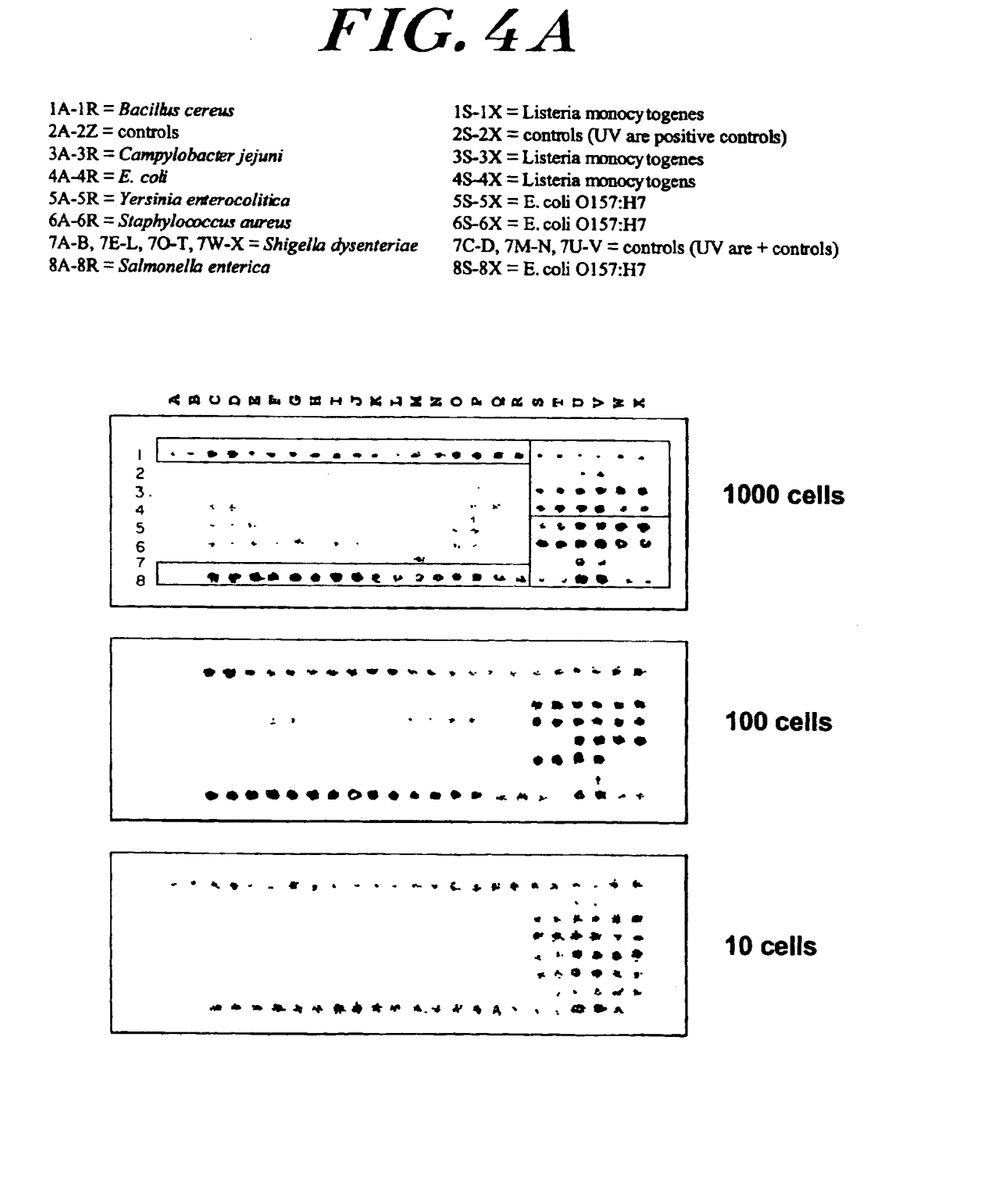
FIG. 4A shows detection results in one embodiment of an array at different species concentrations.

Results from several of the arrays are shown in FIG. 4 for sample levels corresponding to 10, 100 and 1000 cells. The specificity of array detection was demonstrated by the absence of any fluorescent signal above background at any probe address other than that of the target organism. In most of the diluted samples, significant fluorescence was observed at each address for the target organisms in the experiment. At the highest dilutions, fluorescence intensity became undetectable at several addresses, indicating that several specific ones of the target genes were not amplified by PCR with equal efficiency. Nonetheless, fluorescence was still measurable at most addresses specific for a given target organism at target DNA concentrations representing only ten cells of that species.

Discussion

The example confirmed that the multispecies array detects and quantifies the presence of pertinent bacterial species in the targeted range, in many cases with great sensitivity, and that labeling may be effectively performed either during or after amplification. For the organisms where the sensitivity was lower, a preliminary culture step may be used to selectively increase population of those organisms, or the amplification process may be adjusted to augment this component. Alternatively, separate arrays could be provided for different sets of organisms, with the processing cocktails for each one optimized for its subgroup of species.

As described above, systems of the invention include three major components: the sample preparation and DNA amplification system, the array itself, and the image reading or analysis system/software. Applicant contemplates that the sample preparation and DNA amplification system will in general be developed separately and combined for final optimization. Thus, one first identifies a set of preparation steps to carry out fluorescent PCR amplification of target genes from a selected set of microbial populations, examining combinatorial cocktails of primers directed against short oligonucleotides that are unique to or are overrepresented in the genomes of the target model organisms, and identifies cocktails containing sets of primers specific for each gene target. These primers may be tested initially against a model array having only a few target species, using a commercial visible light scanner or an available NIR scanner, as applicable, for image analysis. At this stage, the performance of different fluorescent PCR protocols are evaluated for comparative purposes. During this initial stage, one may also examine the sensitivity and linearity of the array-based testing approach once the fluorescent PCR protocols have been worked out with a model array for analysis. As noted in the example above, adequate sensitivity was observed for most of the initially-selected gene sequences even without optimization.

A preferred sample processing instrument includes a sample chamber with appropriate housings and reagent lines into which a sample of organisms is lysed and in which its DNA adsorbed to a fixed matrix. Once the DNA is immobilized on a solid matrix in the chamber, reagents for washing the adsorbed nucleic acids and for conducting fluorescent PCR amplification are then pumped into the sample chamber in a sequence coordinated with heating cycles. The fluorescent PCR products are then eluted or pumped from the chamber into a chamber housing the array. The fluidics mechanisms, column-housing chamber, lines for reagent streams, and heating-cooling jackets of the instrument for PCR may be similar to those of known micro- or meso-fluidic devices, and are operated under program control to perform both the nucleic acid extraction and the PCR amplification cycling.

Thus, by utilizing a flow cell in which the nucleic acids from the sample can be adsorbed, the system provides efficient and user-friendly sample processing system for quantitatively extracting nucleic acids from the microorganisms for downstream processing in the system. Capillary ports are used to pump reagents into and through the cell to wash the nucleic acids and perform the PCR reactions. "Tuning" of the PCR amplification and labeling system may be accomplished by measuring the efficiency of the extraction fluidics during initial development for performance evaluation of the PCR reaction in the sample cartridge on the model array, for example by using known quantities of model microorganisms such as *E. coli* and *Listeria monocytogenes* in the sample preparation system, and processing conditions are altered, or poorly-amplified sequences are replaced with other sequences, to assure that effective levels of detection are achieved for the full target range. The results reported above for the EXAMPLE indicate feasibility and operability of the simultaneous-array system for pure cultures.

In order to better adapt the preparation and amplification protocol to quantitatively assess the profile of the microbial community present in a specific class of food samples, this parameter is preferably calibrated early in development, and is evaluated at each critical transition step. A first measurement point may be taken after a PCR methodology has been identified, but not necessarily optimized. At this stage, performance of a small model array and manual sample preparation may be assessed with spiked food samples, and may be compared both to results obtained with conventional methods and to the values obtained with pure cultures. Changes to the PCR protocol may be implemented to improve efficiency of, or to replace, ineffective portions of the process. During the transition to successively larger arrays, the efficiency, sensitivity and linearity are similarly evaluated and calibrated. Since one can not possibly test for the same number of species by conventional methods as can large arrays, results from large prototype arrays may be compared to analysis of a few species by conventional methods. This approach identifies performance characteristics such as cross-reactivity and background from food matrix compounds, allowing one to evaluate and correct for these effects, in addition to determining sensitivity.

FIG. 3 illustrates both the method and the overall system or equipment for carrying out the method of the present invention, as applied to testing food products. As shown in FIG. 3, a food sample 1 is first subjected to a preparation and culture step 10. Culture may be carried out manually, or in an automated assembly which basically conditions and places appropriate samples of the food into one or more culture media and incubates or otherwise provides culture conditions appropriate to grow the targeted species or set of species to a suitable population sample size. This may, for example, grow to 50 to 5000 cells or more, and may, for zero tolerance organisms, be optimized to achieve suitable detection levels with as few as ten cells in the sample. The population cultures are then washed, concentrated, lysed or otherwise processed to prepare them as one or more sample DNA aliquots, i.e. groupings of process compatible species, e.g., nucleic acid segments, fragments and components from the species or subgroups of the species, which are loaded in one or more preparation tubes or columns 21 of a processor 20.

As noted above the processing at this stage may be conducted by semi-automated or manual techniques, but is preferably carried out in an automated processor 20 to effect simultaneous PCR amplification of all the target components (or all of one set of PCR-compatible process targets) simultaneously in the tube or column 21. In general, this will be a micro-or-meso-fluidic processing system in which various valves connected to solvent, buffer, reagent and primer supplies, as well as a heater 22, are controlled by a microprocessor to carry out a sequence of washing, blocking or denaturing, attachment of primers, and a number of PCR incubation cycles to amplify and label a set of several target materials simultaneously by polymerase chain reaction and thereby produce effectively detectable quantities of the target nucleic acid sequences present in the sample. The amplified and labeled products are then output to the array hybridization system where the predefined set of probes are allowed to form hydrogen bonds on the corresponding target positions of the prepared array 50, which is fabricated with a matrix of specialized gene targets at predetermined matrix positions on its surface.

In its most general form, applicant contemplates that several different PCR processing regimens may be carried out in parallel, but with different materials and amplification regimens, in separate columns or tubes 21 of the apparatus in order to best amplify the full set of target materials to which the probes of the array 50 are directed. Thus, the optimization processes described above need not result in a single culture cocktail or a single PCR amplification process which is effective to amplify all target materials, but may identify several sets of processing conditions and materials that collectively prepare the sample in one or more subgroups for testing with all probes of the array 50. To this end, the PCR processor 20 may accommodate several tubes 21 simultaneously fed by valved tubing from separate sources of primers and having separately controlled incubation cycles and solvent/reagent mixes. Similarly, the output lines from each of the chambers may feed in parallel to a robot assembly having, for example, a number of parallel pipette spotters individually fed by the different PCR processing chambers and spotted onto different predetermined subsets of the addresses of a single array 50 to test for all the target species. Preferably, however, the process is optimized to process all components together in a single column.

After amplification and deposit on the array, the array 50 is then washed and passes to an array reader 60 which, as noted above, preferably is a visible light or near-IR reader that detects the presence and/or intensity label at each site of the array to identify the presence of bound target material of each type. The array reader 60 provides its output to a microprocessor 70, which may also be programmed to control the operating parameters of the PCR amplification module 20, as well as to record and track the label detection outputs from the reader 60. In general, the basic hardware and equipment of the PCR amplification module 20 may include, or consist largely or entirely of a commercially available or modified microfluidics processing apparatus, having its own microcontroller, and the microprocessor 70 interfaces with that controller to provide the specific operating parameters for specific groups of systems involving simultaneous amplification of the multiple target species of foodborne bacteria as determined by the optimization process outlined above.

Advantageously, the outputs of the array reader 60 include not simply detection at the species level, but distribution of species, as well as genomic variations. Collectively, one complete output set is referred to herein as a "distribution".

In addition to its functions of controlling the process operation and storing the detected distributions, microprocessor 70 preferably includes or connects to a system having a database which may include prior test results, as well as histories, extrinsic parameters and prior correlations or links to any of the foregoing data sets. The histories may include information such as the source of the food components of the product being tested, results of chemical or physical profiles, sensory analyses, and even history such as transportation or shipping conditions. The array outputs may also be corrected, or linked to or grouped based on certain extrinsic and intrinsic properties of the food such as temperature, pH, water activity or ingredient age, and the distributions may be output together with interpretive or comparison data.

In one embodiment, the comparison data includes extrinsic measures of previous test results, such as normative bacteria distributions measured for the same products in different batches, analytic measures such as standard deviations of the distributions of bacterial flora, and other such information. The output data may further include other forms of previously-developed knowledge such as indications of specific conditions (such as off-flavor or color) or indications (such as a prior condition detected during recall following batch release) that may require closer analysis or testing with a different or more inclusive array, or may call for a specific, separate, manual test.

In a preferred implementation of the system, the microprocessor contains a mining and learning database which operates on the output of the array reader 60 to generate or detect relevant higher level information by correlating or comparing the reader output to selected data from the data module, including prior test results, histories and such previously developed correlations. For example, the microprocessor may compare the array reader output to a normative reading, detect an excess of two species or the atypical presence of several other species, then perform a correlation of this sub-group of information to determine, for example, that such a distribution indicates a maladjusted process equipment parameter, or is associated with likely contamination by: yet a fourth organism that has not been tested for. Preferably the data processor 70 also includes an output module and display to output a higher level indication such as a listing of detected species or a population landscape, and to output specific notes on any adverse consequences or process warning indications associated with the detected distribution.

The multispecies arrays of the present invention may be configured for different foods, classes of foods, or processes. Thus, when a non-meat food is being tested, an array that does not include probes specific to meat bacteria may be used. For certain starches and tubers, multiple probes for organisms specific to that class of food materials may be included. Alternatively, the applicant contemplates that after a suitable process of development and checking for cross-reactivities, amplification and extraction efficiencies, a single large array may be fabricated to detect such a great number of species that it may be used for all or most foods. In that case, for any given food, the processor 20 and robotic spotter may be programmed to apply only a subset of their normal operations, for example, to implement only the necessary culture steps and PCR, and to load only the necessary addresses of the array positions for the specific species and gene sequences applicable to the particular class of food sample being tested.

In this manner the invention provides a food monitoring and detection system of enhanced information content and sensitivity which detects not only the presence of deleterious pathogens, but the preconditions, indications and associations that enable or follow from the presence of detected species distributions, and to identify indications of other organisms not specifically probed. It therefore permits the operator to adjust process conditions and prevent undesired occurrences, as well as to develop by data mining and correlation, a proprietary database directed to the proprietor's particular processes and foods for optimizing not only sanitation, but flavor, texture and other less well controlled, more transient or less understood aspects of food quality and food processing, as well as controlling extrinsic factors such as the sources of ingredients.

As noted above, the invention includes an ordered multispecies array with probes for multiple characterizing sequences for each species. The ability to select from a vast number of characteristic sequences is expected to greatly facilitate the process of determining suitable sequences and species groupings for simultaneous PCR amplification. It also allows selection of sequences which may have been largely neglected in conventional bacteriological investigations because their function has not been determined, but which are advantageous in this context because of their efficient amplification and their unique identification with the target species. Thus, the arrays with multi-sequence detection for each of multiple species, offer both high sensitivity and multi-species, or spectral, distribution output.

In addition to food processing, this same system may be applied, by simply selecting a possibly different set of target species and sequences, to carry out environmental, epidemiological, or clinical testing. Thus, for example, rather than testing a food product, the system may be applied to test swabs taken from surfaces or equipment in a slaughterhouse, hospital, kitchen, processing plant or other workplace, or may be applied to samples or cultures taken from groundwater or effluent. Similarly, the species distributions may be selected to assess, for example, specific medical tasks, e.g., to assess respiratory flora to better detect or diagnose the epidemiological patterns of influenza in population centers or to address the possible causative agents for particular presenting symptoms, such as testing CSF for meningitis-like presenting symptoms, or swabs for pneumonia-like presenting symptoms, in a clinic.

In this regard, the test sequences need not be limited to bacterial species and gene sequences, but may include probe sequences for viral, fungal and parasitic organisms and may also include those pathogenic plants. For the different applications, the palette of species may be directed to product-colonizing species, environment or niche-colonizing species, or infectious or chronic mammal-colonizing species. For more specialized clinical applications, the palette may directed to efficiently perform a differential diagnosis of a specific presenting condition or syndrome, for which a recognized set of bacterial, viral or cellular DNA arrays have been selected to rule out or identify the presence of potential etiological factors or determinative agents.

The invention being thus disclosed, further variations and modifications will occur to those skilled in the art, and all such modifications and variations are intended to be within the scope of the invention as described above and defined in the claims appended hereto, and their equivalents.

What is claimed is:

1. A method of food product testing, such method including the steps of selecting a sample of a food product having at least one known organoleptic property;

preparing the sample for assay;

assaying the sample to generate a microbial profile, wherein the assay comprises the step of hybridizing genomic material in the sample to a probe matrix having nucleic acid obtained from a plurality of target species of microorganisms;

forming an output distribution representative of the microbial profile of the sample;

storing the output distribution in a database;

storing data defining a sample profile representative of the at least one known organoleptic property of the sample in the database; and correlating the output distribution with the at least one known organoleptic property, such that the presence of the at least one known organoleptic property can be predicted in another sample of the food product by comparing its microbial profile to the database.

2. The method of claim 1, wherein the step of preparing includes the step of culturing the food sample to increase populations of a plurality of the target species prior to testing with the probe matrix.

3. The method of claim 2, wherein the step of preparing includes the steps of extracting nucleic acid from target organisms, and labeling and amplification of gene regions prior to detection with the probe array.

4. The method of claim 3, wherein the step of labeling is performed after the step of amplification.

5. The method of claim 3, wherein the step of amplification is performed by automated fluidics and incubation to produce output material for detection by the probe matrix.

6. The method of claim 1, wherein the steps of preparing and assaying further comprise utilizing an automated sample preparation and array testing system.

7. The method of claim 1, wherein the step of preparing the sample includes the steps of recovering a plurality of different microorganisms from the food sample, extracting nucleic acids from the plural different microorganisms, and simultaneously amplifying plural target sequences present in the recovered nucleic acids for each of said different microorganisms.

8. The method of claim 1, further comprising the step of storing in the database data of at least one type selected from among (i) other output distributions, (ii) parameters related to the source, condition or processing of food in the sample from which the output distribution was taken, and (iii) parameters related to the source, condition or processing of food in the sample from which other output distributions were taken.

9. A testing method for food quality and processing comprising the steps of selecting a sample of a food product having at least one known organoleptic property;

preparing an array having a plurality of probes, each probe being directed to multiple gene sequences from a plurality of different target species of organisms;

preparing a sample of the food product, wherein the step of preparing a sample includes extracting nucleic acids from the sample;

amplifying the extracted nucleic acids such that target sequences are preferentially amplified;

hybridizing the amplified nucleic acids to the probes on the array;

forming an output distribution representative of the plurality of target species of organisms present in the sample;

storing the output distribution and information related to the at least one known organoleptic property of the sample in a database; and correlating the output distribution with the at least one known organoleptic property such that the presence of the at least one known organoleptic property can be predicted in another sample of the food product by comparing its output distribution to the database.

10. The testing method of claim 9, wherein the species are foodborne species affecting food quality.

11. The testing method of claim 9, wherein the target sequences include species sequences coding for factors involved in pathogenesis or virulence factors.

12. The testing method of claim 9, wherein the target sequences are species sequences selected for efficient amplification as a group.

13. The testing method of claim 9, wherein the array tests for a palette of species selected from among product colonizing species, environment colonizing species, and mammalian colonizing species.

14. The testing method of claim 9, further comprising the step of displaying the output distribution with a note describing adverse consequences or process warning indications associated with the detected distribution.

15. The testing method of claim 9, wherein the target sequences are species sequences selected for probe hybridization and detection as a group.

16. The testing method of claim 9, further including the steps of determining sensitivity and cross reactivity of the array.

17. The testing method of claim 9, wherein the output distribution indicates the quantity of each target species present in the sample.

18. The method of claim 1, wherein the at least one known organoleptic property is selected from the group consisting of smell, texture, and taste.

19. The method of claim 1, wherein the method further comprises correlating the output distribution with processing conditions.

20. The method of claim 19, wherein processing conditions are selected from the group consisting of the source of a component, flavor potential, and shelf-life.

21. The testing method of claim 9, wherein the at least one known organoleptic property is selected from the group consisting of smell, texture, and taste.

22. The testing method of claim 9, wherein the method further comprises correlating the output distribution with processing conditions.

23. The testing method of claim 22, wherein processing conditions are selected from the group consisting of the source of a component, flavor potential, and shelf-life.

* * * * *